United States Patent [19]

Sylvia et al.

[11] Patent Number: 5,096,481
[45] Date of Patent: Mar. 17, 1992

[54] SHEARED ROOTS AS A VA-MYCORRHIZAL INOCULUM AND METHODS FOR ENHANCING PLANT GROWTH

[75] Inventors: David M. Sylvia; Amiel G. Jarstfer, both of Gainesville, Fla.

[73] Assignee: University of Florida, Gainesville, Fla.

[21] Appl. No.: 574,763

[22] Filed: Aug. 30, 1990

[51] Int. Cl.$^5$ .............................. A01N 63/04
[52] U.S. Cl. .............................. 71/65; 71/5; 47/1.1; 47/58; 435/254
[58] Field of Search .................. 71/65, 77, 79, 5; 47/1.1, 58; 435/254

[56] References Cited

U.S. PATENT DOCUMENTS 4,551,165  11/1985  Warner ............................ 71/24

OTHER PUBLICATIONS

Graham J. H. et al., "Innoculation of Citns with Root Fragments containing Chlamydospores..." etc. Canadian J. Bot., vol. 64, pp. 1739-1744, 1986.
Jefferies, "Use of Mycorrhizae in Agriculture", CRC Critical Reviews in Biotechnology, vol. 5, Issue 4(1987) pp. 319-357.
Walker et al. "Sodium Alginate for Prod. and Formulation...", Weed Science, vol. 31:333-338, 1983.
Hung et al., "Production of Vesicular-Arbuscular Mycorrhizal Fungus Innorulum...", Applied and Environ. Microbiol. vol. 54, No. 2, Feb. 1988, pp. 353-357.

Primary Examiner—Richard L. Raymond
Assistant Examiner—B. Bembenick
Attorney, Agent, or Firm—Kerkam, Stowell, Kondracki & Clarke

[57] ABSTRACT

A vesicular-arbuscular mycorrhizal inoculum composition comprising host plant roots colonized by at least one species of vesicular-arbuscular mycorrhizal fungus, the colonized roots having a particle size in the range of from about 33 μm to about 425 μm and a propagule density of up to about 1,000,000 vesicular-arbuscular mycorrhizal fungi propagules per gram dry mass of host plant root; methods for the encapsulation thereof and methods for enhancing plant growth utilizing the inocula.

20 Claims, 1 Drawing Sheet

SHEARED ROOTS AS A VA-MYCORRHIZAL INOCULUM AND METHODS FOR ENHANCING PLANT GROWTH

BACKGROUND OF THE INVENTION

1. Field of the Invention

The present invention relates to a vesicular-arbuscular mycorrhizal fungi inoculum and methods for the production and the utilization thereof for plant growth enhancement.

2. Discussion of the Prior Art

VA (vesicular-arbuscular) mycorrhizal fungi are beneficial fungi in that they infect the feeding roots of plants and stimulate uptake of phosphorus from the soil. Hyphae of the fungus grow outwardly from the root well beyond the phosphate depletion zone (the zone from which the available phosphate has already been consumed by the plant). Selected VA-mycorrhizal fungi have been shown to enhance the growth of numerous plants of economic importance [Jeffries, *CRC Critical Reviews in Biotechnology*, Vol. 5, "Use of Mycorrhizae in Agriculture," pages 319-357 (1987)], including vegetables [Haas et al, *Agron. J.*, Vol. 79, "Vesicular-arbuscular Mycorrhizal Fungus Infestation and Phosphorus Fertigation to Overcome Pepper Stunting After Methyl Bromide Fumigation," pages 905-910 (1987); Mohandas, *Plant and Soil*, Vol. 98, "Field Responses to Tomato (*Lycopersicon esculentum*) to Inoculation With a VA-mycorrhizal Fungus *Glomus fasciculatum* and *Azotobacter virelandii*, pages 295-297 (1987); Plenchette et al, *Plant and Soil*, Vol. 70, "Growth Response of Several Plant Species to Mycorrhizae in a Soil of Moderate Phosphorus Fertility I. Mycorrhizal Dependency Under Field Conditions," pages 197-209 (1983)]; field crops [Baltruschat, *Zeitschrift für Pflanzenkrankheiten und Pflanzenschutz*, Vol. 94, "Field Inoculation of Maize with Vesicular-arbuscular Mycorrhizal Fungi by Using Expanded Clay as Carrier Material for Mycorrhiza," pages 419-430 (1987); Hall, *J. Agr. Sci.*, Vol. 102, "Field Trials Assessing the Effect in Inoculating Agricultural Soils With Endomycorrhizal Fungi," pages 725-731 (1984); Medina et al, *Biol. Fert. Soils*, "Growth Response of Field-grown Siratro (*Macroptilium atropurpureum* Urb.) and *Aeschynomene americana* L. to Inoculation With Selected Vesicular-arbuscular Mycorrhizal Fungi," Vol. 9, pages 54-60 (1990)] and native plants used for revegetation [Dehgan et al, Bartow, Fla.: Florida Institute of Phosphate Research, "Propagation and Mycorrhizal Inoculation of Indigenous Florida Plants for Phosphate Mine Revegetation, No. 03-053-076, 225 pages (1989); Sylvia, *J. Coastal Res.*, Vol. 5, "Nursery Inoculation of Sea Oats with Vesicular-arbuscular Mycorrhizal Fungi and Outplanting Performace of Florida Beaches," pages 747-754 (1989)]. Nonetheless, VA-mycorrhizal fungi are not used widely in crop production, partially because inoculum sources are limited and application technologies are not well developed.

A major limitation to the utilization of VA-mycorrhizae in crop production is the inability to produce sufficient amounts of fungal inoculum. The VA-mycorrhizal fungi have not been grown successfully in pure culture and are considered obligate symbionts [Hepper, *VA Mycorrhiza*, Powell and Bagyaraj, eds. (CRC Press, Boca Raton, Fla. (1984))]. Due to this limitation, these fungi are usually maintained and increased in pot cultures [Ferguson et al, "Methods and Principles of Mycorrhizal Research," N. C. Schenck, ed. (American Phytopathological Society, St. Paul, Minn. (1982))], sand [Thompson, *Can. J. Bot.*, Vol. 64, pages 2282-2294 (1986)] or expanded clay [Dehne et al, *Zeitschrift für Pflanzenkrankheiten und Pflanzenschutz*, Vol. 93, No. 4, pages 415-424 (1986)]. Pot cultures are comprised of host plants, mycorrhizal fungi and soil microflora and microfauna, and are influenced by the physical and chemical properties of the potting medium [Sylvia, "Applications of Mycorrhizal Fungi In Crop Production," J. J. Ferguson, ed. (University of Florida, Gainesville, Fla. (1984))]. It is not surprising that the quality and quantity of propagules produced for inoculum by this method varies widely due to the many interactions among these variables.

Inoculum of VA-mycorrhizal fungi may consist of soil (containing colonized root fragments, spores and hyphae), colonized roots alone or spores alone. The use of soil and root inoculum has limited commercial value because these systems can become easily contaminated by other VA-mycorrhizal fungi and plant pathogens [Schenck et al, *Phytopathology*, Vol. 72, page 950 (1982)]. Single-species cultures of VA-mycorrhizal fungi that are relatively free of other contaminating organisms are best achieved by the use of spore inoculum.

Several alternatives to the pot-culture system have been proposed for inoculum production. The VA-mycorrhizae have been formed on root-organ cultures [Mosse et al, *Physiol. Plant Pathology*, Vol. 5, page 215 (1975); Miller-Wideman et al, *Can. J. Microbiol.*, Vol. 30, page 642 (1984)]. However, colonization and sporulation are limited in these monoxenic systems. The VA-mycorrhizae have also been established in solution culture [Howeler et al, *New Phytol.*, Vol. 90, page 229 (1982); Mosse et al, *Can. J. Bot.*, Vol. 62, page 1523 (1984); Elmes et al, *Can. J. Bot.*, Vol. 62, page 1531 (1984); Crush et al, *N. Z. J. Agricultural Research*, Vol. 24, page 371 (1981); U.S. Pat. No. 4,294,037]. For example, Elmes and Mosse reported approximately 50% colonization of *Zea mays* roots after nine weeks in a nutrient film system. The inoculum produced in their nutrient system, however, was primarily colonized root material. In general, sporulation in solution culture systems has been poor. This is due to the fact that VA-mycorrhiza are inhibited by excessive moisture and poor aeration in the natural environment.

The VA-mycorrhizae have also been grown in aeroponic culture [Hung et al, *Appl. Environ. Microbiol.*, Vol. 54, "Production of Vesicular-arbuscular Mycorrhizal Fungus Inoculum in Aeroponic Culture," pages 353-357 (1988)].

Various strategies have been proposed to apply inoculum of VA-mycorrhizal fungi in agriculture [Jarstfer et al, *Soil Microbial Technologies*, B. Metting, ed. (Marcel Dekker, Inc.), "Inoculation Techniques and Inoculum Production of Vesicular-arbuscular Mycorrhizal Fungi" (in press)]. Inocula-containing soil is considered impractical due to its bulk and the risk of contamination; however, chopped roots in peat blocks [Warner, U.S. Pat. No. 4,551,165, "Mycorrhizal Seed Pellets" (1985)] and spores within a porous matrix [Baltruschat, supra] have been proposed for field application. Since the cost of inoculum production is high, a need exists for methods to process inocula of VA-mycorrhizal fungi for efficient distribution.

Colonized roots of a Glomus sp. can serve as effective inoculum due to the presence of intraradical vesicles [Biermann et al, *New Phytol.*, Vol. 95, "Use of Vesicular-arbuscular Mycorrhizal Roots, Intraradical Vesicles and Extraradical Vesicles As Inoculum," pages 97-106 (1983)]. However, for efficient handling inoculum should be processed into small and uniform pieces. Such inoculum can then be pelletized [Crush et al, *Endomycorrhizas*, Sanders and Mosse, eds. (Academic Press, N.Y.), "Preliminary Results on the Production of Vesicular-arbuscular Mycorrhizal Inoculum by Freeze Drying" (1975)] or used in fluid-drill systems [Bryan, *Applications of Mycorrhizal Fungi in Crop Production*, J. Ferguson, ed. (University of Florida, Gainesville, Fla.), "Fluid Drilling of Vegetable Crops: A Technique Adaptable for Mycorrhizal Field Inoculation," pages 46-47 (1984)]. Roots colonized by a Glomus sp. have been macerated [Biermann et al, supra] and variously milled [Warner, supra; Jackson et al, *Soil Sci. Soc. Amer. Proc.*, Vol. 36, "Effects of Vesicular-arbuscular Mycorrhizae on Growth and Phosphorous Content of Three Agronomic Crops," pages 64-67 (1972)]. However, milling was found to reduce inoculum potential. Warner, supra, reported nearly a 50% drop in propagules when air-dried peat inoculum was milled to a size of 850 $\mu$m.

It is an object of the present invention to provide a novel VA-mycorrhizal inoculum composition which is advantageously applied in agricultural methods for enhancing plant growth and which has a high propagule density.

SUMMARY OF THE INVENTION

The foregoing and other objects are realized by the present invention, one embodiment of which is a vesicular-arbuscular mycorrhizal inoculum composition comprising host plant roots colonized by at least one species of vesicular-arbuscular mycorrhizal fungus, the colonized roots having a particle size in the range of from about 33 $\mu$m to about 425 $\mu$m and a propagule density of from about 10,000 up to about 1,000,000 vesicular-arbuscular mycorrhizal fungi propagules per gram dry mass of host plant root.

A further embodiment of the invention is the above inoculum composition encapsulated in a biodegradable material suitable as a carrier in a composition adapted for enhancing plant growth.

An additional embodiment of the invention relates to a method of producing the above-described vesicular-arbuscular mycorrhizal inoculum composition comprising providing host plant roots colonized by at least one species of vesicular-arbuscular mycorrhizal fungus and reducing the colonized roots to particles having a size in the range of from about 33 $\mu$m to about 425 $\mu$m, the particles having a propagule density of from about 10,000 up to about 1,000,000 vesicular-arbuscular mycorrhizal fungi propagules per gram of host plant root.

Yet a further embodiment of the invention comprises a method of enhancing plant growth comprising effecting the growth of plants in the presence of an amount of the above-described inoculum compositions sufficient to stimulate the uptake by the plants of phosphorus from the soil.

DETAILED DESCRIPTION OF THE INVENTION

Figure 1:
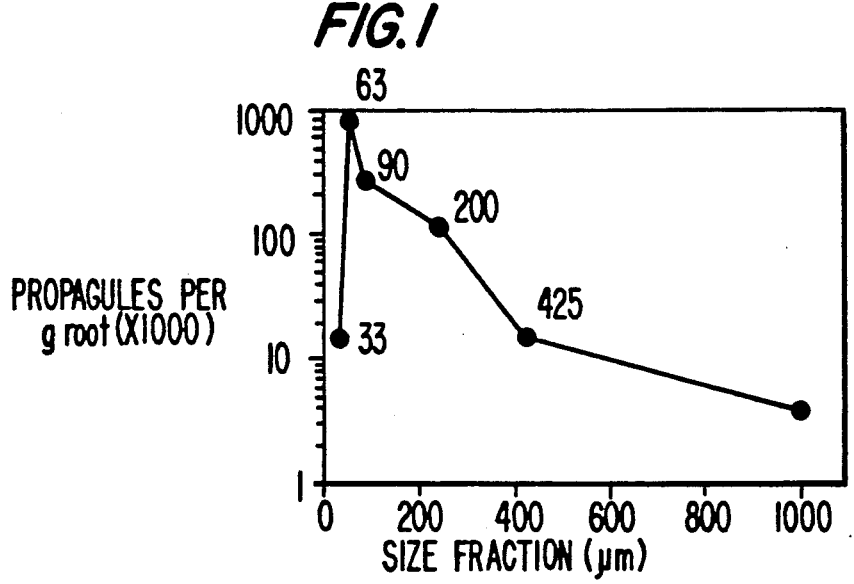
FIG. 1 is a graphical depiction of the fungus propagule density as a function of particle size of the inoculum of the invention.

The present invention is predicated on the discovery that VA-mycorrhizal fungi colonized host plant roots which are reduced in size in such a manner as to produce a product having a particle size in the range of from about 33 $\mu$m to about 425 $\mu$m and about 10,000 up to about 1,000,000 VA-mycorrhizal fungi propagules per gram dry mass of host plant root comprise an effective plant growth enhancing agent which is advantageously and efficiently stored, transported and applied in agricultural methods.

It has been unexpectedly found that subjecting colonized roots to methods of size reduction which involve subjecting, e.g., liquid suspensions of the roots to a high shear size reduction process in liquid, the size of the colonized roots may be reduced to between 33 $\mu$m and 425 $\mu$m while actually increasing the fungi propagule density thereof. At particle sizes below about 33 $\mu$m, the fungi propagule density of the roots begins to fall off dramatically, but is still greater than that of unprocessed roots. It will be understood by those skilled in the art that any size reduction process may be employed which results in a "cutting" of the roots rather than a grinding or crushing of the tissue.

It will be recognized by those skilled in the art that any host legume, cereal, grass, vegetable crop or other herbaceous or woody plant root can be employed for colonization of the VA-mycorrhizal fungi. Exemplary of such plants are *Phaseolus vulgaris, Allium porrum, Avena sativa, Zea mays, Lycopersicon esculentum* and *Triticum aestivum*.

The fungus employed to colonize the roots may be selected from any of the genera of VA-mycorrhizal fungi that form vesicles in roots, including Glomus, Acaulospora, Entrophospora or Sclerocystis.

Although any conventional system and method for colonizing the roots may be employed, it is preferred to employ the aeroponic culture system described by Hung et al (1988), supra. This is because roots grown in aeroponic cultures are free of debris that would reduce the efficiency of shearing.

Briefly, "aeroponic culture" includes any system or zone comprising a highly aerobic mist or vapors of an aqueous solution of nutrients capable of maintaining the growth of the root system of a plant root system and a VA-mycorrhizal fungus thereon. It is essential that the mist or vapors be highly aerated.

The nutrient mist or vapors may be generated according to any conventional method for generating mists. For example, a system employing an atomizer such as that described by Went [*The Experimental Control of Plant Growth*, Chronica Botanica Co., Waltham, Mass., pages 81-83 (1957)] may be employed for obtaining the aeroponic culture. In addition, the systems described by Vyvyan et al ["A Method of Growing Trees With Their Roots in a Nutrient Mist," *Ann. Rep. East Malling. Res. Sta.*, pages 95-98 (1953)]; Klotz [*Phytopathology*, Vol. 34, pages 507-508 (1944)] and Carter [*Phytopathology*, Vol. 32, pages 623-625 (1942)] may also be employed.

The nutrient mist or vapors may also be generated by employing a modified version of the system described by Zobel et al [*Plant Physiol.*, Vol. 57, pages 344–346 (1976)].

The colonized roots are harvested and cut to appropriate lengths for convenience, i.e., 0.75 cm to about 1.5 cm, and then mixed with water. Roots may also be used uncut. Generally, the ratios of colonized roots to water may vary from about 1 g fresh weight to about 10 g fresh weight per 50 ml of water.

The suspension of colonized roots is then subjected to the above-described conditions of high shear for a time sufficient to reduce the size of the roots to the desired particle size.

The optimum particle size, i.e., the size at which the fungus propagule density is highest, is about 63 μm. It will be understood, however, that any fraction from about 33 μm to about 425 μm may be employed. For example, fractions wherein the particle size ranges from about 60 μm to about 250 μm, from about 33 μm to about 60 μm, or most preferably from about 60 μm to about 90 μm, may also be employed.

The reduced colonized roots are harvested and employed directly in an agricultural method, for example, encapsulation in a biodegradable material which facilitates the harvesting, storage, delivery, transport and field application of the inoculum. The inoculum composition may be encapsulated according to any conventional encapsulation technique, which forms no part of the present invention.

Suitable encapsulants include any material which will protect the fungi from environmental or physical damage and which is capable of encapsulating the inoculum, but which is relatively easily biodegraded after application in the field to release the contained inoculum. Suitable encapsulants include carrageenan, hydroxyethylcellulose, alginates and gum arabic.

The inocula or encapsulated material may be incorporated in any plant growth medium, culture or system to enhance the growth of plants therein. Each may be formulated with at least one viable propagule of a host plant to form an association which will enhance the growth of the resultant plant. It will be understood by those skilled in the art that the term "propagule" refers to a seed or any other reproductive part of a plant.

The invention is illustrated by the following non-limiting examples. In the examples, roots colonized by VA-mycorrhizal fungi in an aeroponic chamber are harvested, blotted dry and cut into 1 cm lengths. The aeroponic culture system is described by Hung et al (1988), supra. Colonized root pieces are placed in water and processed into a slurry with a food processor. In the examples herein, roots of sweet potato (*Ipomoea batatas* (L.) Lam, cv. "White Star" were colonized with a Glomus sp. Five grams of roots were placed in 50 ml of distilled water in the work bowl of a "Little Pro" food processor (Cuisinart) and processed for up to 80 seconds. Processing was interrupted half-way through each run or every 10 seconds and roots adhering to the side of the bowl were scraped back into the water.

Using this process, up to 1,000,000 propagules of VA-mycorrhizal fungi per gram of dry mass root were achieved. After processing, the propagules can be encapsulated, incorporated into a hydrogel to enhance inoculum delivery or mixed directly in the growing medium. The novel and unexpected aspect of the results of the examples herein is that the propagule density of the inoculum increased dramatically in the size fractions down to about 63 μm.

EXAMPLE 1

Aeroponically grown roots of sweet potato colonized with an undescribed Glomus sp. (isolate S328) were harvested from an eighteen-week-old aeroponic chamber. Roots were blotted with paper towel and scissor-cut into 1 cm lengths, and fresh and dry masses were determined on a portion of the material. Six 5 gram sub-samples were processed for 40 seconds with 50 ml of distilled water. Processing was interrupted every 10 seconds to scrape roots back into the water. The scissor-cut material was also mixed with 50 ml of water.

Size fractionation was accomplished by washing the contents of the food processor work bowl over a stack of four sieves that had openings from 425 μm to 63 μm. The smallest fraction was collected on 33 μm polyester mesh. The root material from each fraction was collected and known amounts (dry weight basis) were added to the first dilution of a most probable number (MPN) [Porter, *Aust. J. Soil Res.*, Vol. 17, "The 'Most Probable Number' Method for Enumerating Infective Propagules of Vesicular Arbuscular Mycorrhizal Fungi in Soil," pages 515–519 (1979)] assay as follows: for the scissor-cut, >425 and 425 μm to 250 μm fractions, the root material was collected by vacuum filtration to remove excess water and weighed directly for additions to the growth medium. For the 250 to 90, 90 to 63 and 63 to 33 fractions, the root material was collected by vacuum filtration and resuspended in 50 ml of water. Sub-samples for addition to the MPN test and for dry mass determination were removed from a stirred suspension of each fraction. Three 10-fold dilutions of processed roots were made in Metro-Mix 200 ® (W. R. Grace & Co.) beginning at 1:3529 (w/v). Fifty milliliters of each dilution were added to each of five "Pinecell" Conetainers ® (63 ml capacity, Ray Leach Conetainer Nursery), five surface-disinfested (15 min. in 25% Chlorox) seeds of sea oats (*Uniola paniculata* L.) were added to each Pinecell and covered with fine horticultural vermiculite. Plants were grown in the high-intensity-discharge (HID) growth chamber for 42 d, at which time complete root systems were harvested and assessed for colonization by VA-mycorrhizal fungi.

Propagule density increased dramatically with decreasing size fraction down to about 63 μm, after which propagule density decreased sharply (see FIG. 1). The distribution of total dry mass in each fraction was 17, 63, 11, 3 and 5%, respectively, for the >425, 425 to 250, 250 to 90, 90 to 63, and 63 to 33 μm fractions. The overall yield (weighted mean) of inoculum was 135,380 propagules $g^{-1}$ dry mass of root. The propagule density of non-processed roots is equivalent to the 1,000 fraction (i.e., scissor-cut roots) depicted in FIG. 1.

EXAMPLE 2

Sweet potato roots harvested from a 13-week-old aeroponic culture as in Example 1 were stored at 4° C. for 51 d and then processed for 40 seconds. The inoculum was fractionated over metal sieves. The fraction between 90 μm and 250 μm was washed over GA4-S, 0.8 μm pore size Metricel ® membranes (Gelman Sciences, Inc.) with sterile water or a disinfecting solution (2% chloramine T plus 0.02% streptomycin sulfate). This material was then suspended in 2.5% Kappa-carrageenan (C-1263, Sigma). The carrageenan was prepared by dissolving in warm water and then autoclaving at 121° C. for 20 minutes. The solution was cooled to 28° C. in a water bath and pellets were produced by extruding the carrageenan suspension through a 16-gauge needle from a 30 ml syringe into 0.3M KCl at room temperature. Pellets were separated from the KCl by sieving over a surface-disinfested 425 μm metal sieve and were then blotted on sterile paper towels. Pellets were stored at 4° C. in plastic bags. A bioassay for infectivity was conducted in the HID growth chamber. Thirty milliliters of Metro-Mix 200® were placed in each Pinecell. Pellets (5, 10 or 15) were placed on the growth medium and an additional 20 ml of growth medium were added to five replicated per treatment. Five surface-disinfested seeds of sea oats were placed in each Pinecell and covered with vermiculite. Plants were watered with 0.25 strength Hoagland's solution [Hoagland et al, California Agricultural Experimental Station Circular No. 347 (University of California, Berkeley, Calif.), "The Water Culture Method For Growing Plants Without Soil," pages 1-32 (1950)] for the first four weeks of the assay and deionized water during the final two weeks. The assay was harvested after six weeks of growth in the growth chamber and the MPN of propagules per pellet was determined.

EXAMPLE 3

Encapsulation was also tested with a second VA-mycorrhizal fungus. Sweet potato roots colonized with *Glomus etunicatum* Becker and Gerdemann (isolate S329) were grown in aeroponic culture for eighteen weeks, colonized roots were processed for forty seconds and the fraction between 63 and 90 μm was collected on metal sieves and washed with water onto a Metricel® membrane. This material was then suspended in 2.5% carrageenan. The carrageenan pellets were prepared as above, except that the solution was cooled to 34° C. in a water bath. The infectivity assay was conducted in Pinecells using *Zea mays* L. var. 'Early Sunglow' (W. Atlee Burpee Co.) as the host and pasteurized Arredondo loamy sand (loamy, siliceous, hyperthermic, Grossarenic Paleudult) as the growth medium. Seven replicates of 0, 1, 5, 10 or 20 pellets were placed on 30 ml of soil and covered with an additional 20 ml of soil. Two seeds were placed on the soil surface and covered with vermiculite. The assay was harvested after six weeks of growth in the HID growth chamber and the MPN of propagules per pellet was determined.

Figure 2:
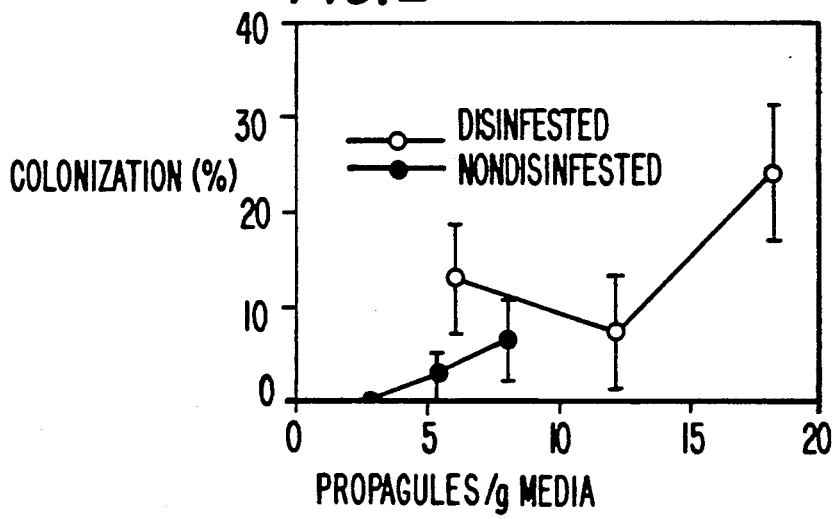
FIGS. 2 and 3 are graphical depictions of colonization of the inocula of the invention as a function of the fungi propagule density.

Processed roots were encapsulated successfully in carrageenan. For *Glomus* sp. (S328), the disinfested inoculum contained 1.2 propagules per pellet while the non-disinfested inoculum contained 0.5 propagules per pellet. Increasing the density of encapsulated inoculum resulted in improved colonization (see FIG. 2). For *G. etunicatum*, the inoculum contained 0.3 propagules per pellet although each had an average of $4.0 \pm 0.85$ spores per pellet.

EXAMPLE 4

Sweet potato roots colonized by *Glomus* sp. (S328) as in Example 1 were harvested from an 8.5-week-old aeroponic culture and processed forty seconds. The fraction between 90 and 425 μm was used to make dilutions in a 2.5% hydroxyethylcellulose carrier (Natrosol®). The dilutions resulted in concentrations of 0, 0.1, 0.5, 1, 10 and 100 spores ml$^{-1}$. A no-gel control was also established.

A six-week bioassay was conducted in the growth chamber. Thirty milliliters of Metro-Mix 200® were placed in a Pinecell, 1 ml of an inoculum suspension was added and this was covered with an additional 20 ml of growth medium. There were seven replicates per treatment. Seeds of sea oats were placed on the surface of the medium and covered with vermiculite. Plants were watered with 0.25-strength Hoagland's solution (Hoagland, supra) for the first four weeks of the assay and deionized water during the final two weeks. The MPN of propagules in the initial inoculum was determined.

Figure 3:
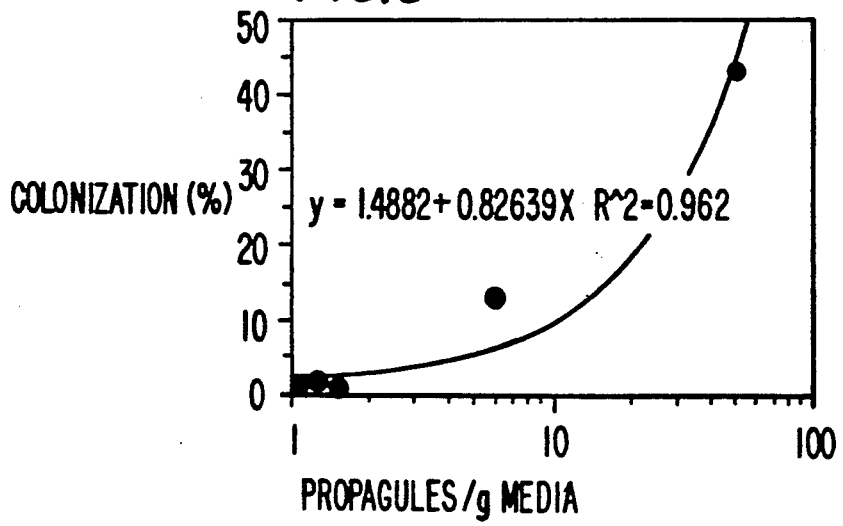

Natrosol® served as an effective carrier of processed inoculum. The inoculum contained 0.5 propagules ml$^{-1}$ and increasing inoculum density resulted in increased colonization (see FIG. 3).

We claim:

1. A vesicular-arbuscular mycorrhizal inoculum composition produced by reducing host plant roots colonized by at least one species of vesicular-arbuscular mycorrhizal fungus, in size, by a high shear size reduction process in a liquid to colonized roots having a particle size in the range of from about 33 μm to about 425 μm and a propagule density of up to about 1,000,000 vesicular-arbuscular mycorrhizal fungi propagules per gram dry mass of host plant root.

2. A composition according to claim 1, wherein said fungus is of the genera Glomus, Acaulospora, Entrophospora or Sclerocystis.

3. A composition according to claim 2, wherein said fungus is a Glomus sp.

4. A composition according to claim 1, wherein said host plant is a grass, vegetable crop or other herbaceous plant, a legume or a woody plant.

5. A composition according to claim 1, wherein said colonized roots have a particle size in the range of from about 33 μm to about 60 μm.

6. A composition according to claim 1, wherein said colonized roots have a particle size in the range of from about 60 μm to about 250 μm.

7. A composition according to claim 1, wherein said colonized roots have a particle size in the range of from about 60 μm to about 90 μm.

8. A composition according to claim 1, wherein said colonized roots have a particle size of about 63 μm.

9. An inoculum composition of claim 1 encapsulated in a biodegradable material suitable as a carrier in a composition adapted for enhancing plant growth.

10. A composition according to claim 9, wherein said encapsulant material is carrageenan, hydroxyethylcellulose, an alginate or gum arabic.

11. A method of producing a vesicular-arbuscular mycorrhizal inoculum composition comprising providing host plant roots colonized by at least one species of vesicular-arbuscular mycorrhizal fungus and reducing said colonized roots by a high shear size reduction process in a liquid to particles having a size in a range of from about 60 μm to about 425 μm, said particles having a propagule density of up to about 1,000,000 vesicular-arbuscular mycorrhizal fungi propagules per gram dry mass of host plant root.

12. A method according to claim 11, wherein said colonized roots have a size in a range of from about 0.75 cm to about 1.5 cm prior to being reduced in size to said particles.

13. A method according to claim 11, wherein said fungus is of the genera Glomus, Acaulospora, Entrophospora or Sclerocystis.

14. A method according to claim 13, wherein said fungus is a Glomus sp.

15. A method according to claim 11, wherein said host plant is a grass, vegetable crop or other herbaceous plant, a legume or a woody plant.

16. A method of enhancing plant growth by increasing vesicular-arbuscular mycorrhizal fungus colonization on plant roots comprising effecting the growth of plants in the presence of an amount of an inoculum composition of claim 1 or 2 sufficient to stimulate the uptake by said plants of available phosphorus from the soil.

17. A method according to claim 16, wherein said colonized roots have a particle size in the range of from about 33 $\mu$m to about 425 $\mu$m.

18. A method according to claim 16, wherein said colonized roots have a particle size in the range of from about 60 $\mu$m to about 90 $\mu$m.

19. A method according to claim 16, wherein said colonized roots have a particle size in the range of from about 33 $\mu$m to about 60 $\mu$m.

20. A method according to claim 16, wherein said colonized roots have a particle size of about 63 $\mu$m.

* * * * *

UNITED STATES PATENT AND TRADEMARK OFFICE
CERTIFICATE OF CORRECTION

PATENT NO. : 5,096,481

DATED : March 17, 1992

INVENTOR(S) : David M. SYLVIA, ET AL

It is certified that error appears in the above-identified patent and that said Letters Patent is hereby corrected as shown below:

On the title page, under the heading "Other Publications" at line 1: delete "Innoculation of Citns" and substitute -- Inoculation of substitute -- Inoculation of Citrus --.

On the title Page, in column 2 at line 6: delete "Innorulum" and substitute -- Inoculum --.

Signed and Sealed this

First Day of June, 1993

Attest:

MICHAEL K. KIRK

Attesting Officer

Acting Commissioner of Patents and Trademarks